(12) United States Patent
Gamage et al.

(10) Patent No.: US 8,121,867 B2
(45) Date of Patent: Feb. 21, 2012

(54) SOFTWARE APPLICATION GENERATION AND IMPLEMENTATION METHOD AND SYSTEM

(75) Inventors: Brian James Gamage, Middletown, MD (US); Julian I. Kamil, Gaithersburg, MD (US); William Philip Shaouy, Atlanta, GA (US)

(73) Assignee: International Business Machines Corporation, Armonk, NY (US)

( * ) Notice: Subject to any disclaimer, the term of this patent is extended or adjusted under 35 U.S.C. 154(b) by 296 days.

(21) Appl. No.: 12/431,245

(22) Filed: Apr. 28, 2009

(65) Prior Publication Data

US 2010/0274681 A1    Oct. 28, 2010

(51) Int. Cl.
*G06Q 50/00* (2006.01)
(52) U.S. Cl. .......................................................... 705/3
(58) Field of Classification Search .................. 701/207, 701/208, 213, 214; 705/2–5; 707/999.003, 707/999.007; 709/203, 217, 999.007
See application file for complete search history.

(56) References Cited

U.S. PATENT DOCUMENTS

| | | | |
|---|---|---|---|
| 6,377,961 B1 | 4/2002 | Ryu | |
| 6,415,227 B1 | 7/2002 | Lin | |
| 6,826,537 B1 | 11/2004 | Wood et al. | |
| 7,248,688 B2 * | 7/2007 | Wellons et al. | 379/265.1 |
| 7,752,060 B2 * | 7/2010 | Hicks et al. | 705/3 |
| 7,835,923 B1 * | 11/2010 | Rowley | 705/2 |
| 7,890,581 B2 * | 2/2011 | Rao et al. | 709/204 |
| 2004/0172282 A1 | 9/2004 | Benja-Athon | |
| 2006/0149590 A1 | 7/2006 | Palmer et al. | |
| 2008/0270180 A1 | 10/2008 | Sholtis et al. | |
| 2009/0024416 A1 | 1/2009 | McLaughlin et al. | |

FOREIGN PATENT DOCUMENTS

| | | |
|---|---|---|
| WO | 2008079341 A2 | 7/2008 |
| WO | 2008079341 A3 | 7/2008 |

OTHER PUBLICATIONS

Computer Science Spotlight Presentation: Using mashups to coordinate healthcare; (Transcript 6 pages plus cover page Jan. 8, 2009). http://w3.tap.ibm.com/medialibrary/media/view?id=37541. The transcript presented there lays out a high-level intention to do some of what we describe in this invention, but uses different component technology components in some areas and is not at a point where it is designed yet.

* cited by examiner

*Primary Examiner* — Andrew Joseph Rudy
(74) *Attorney, Agent, or Firm* — Schmeiser, Olsen & Watts; William Schiesser

(57) ABSTRACT

An application generation and implementation method and system. The application generation method includes generating and storing a transparency software application comprising multiple application software code. The application implementation method includes retrieving by the transparency software application, personal data and an address associated a point of interest associated with a user. The two dimensional mapping application is enabled and a geographical map and selections for relevant healthcare service providers specified on the geographical map are received. The transparency software application retrieves ratings and feedback data and a selection for filter criteria. The filter criteria and subsequent filter criteria are evaluated and in response a report indicating results of the evaluation is generated and stored.

20 Claims, 5 Drawing Sheets

SOFTWARE APPLICATION GENERATION AND IMPLEMENTATION METHOD AND SYSTEM

FIELD OF THE INVENTION

The present invention relates to a method and associated system for generating and implementing a transparency software application.

BACKGROUND OF THE INVENTION

Generating code typically comprises a complicated and inefficient process with little flexibility. Code developers are typically required to generate multiple versions of code which is costly and very time consuming. Each of the multiple versions of code is independently generated.

SUMMARY OF THE INVENTION

The present invention provides a method comprising:
enabling, by a computing device for a first user, access to a transparency software application, said transparency software application executed by a computer processor of said computing device;
retrieving, by said transparency software application from a personalization engine, personal data associated with said first user;
transmitting, by said transparency software application to said first user, a first request for a point of interest associated with said first user;
receiving, by said transparency software application from said first user in response to said first request, an address associated with said point of interest;
enabling, by said transparency software application in response to said receiving said address, a two dimensional mapping engine;
receiving, by said transparency software application from said two dimensional mapping engine, a geographical map associated with said address;
receiving, by said transparency software application from said first user, selections for relevant healthcare service providers specified on said geographical map;
retrieving, by said transparency software application from a ratings and feedback engine, ratings and feedback data associated with said relevant healthcare service providers;
receiving, by said transparency software application from said first user, a selection for a first filter criteria;
first evaluating, by said transparency software application, said first filter criteria;
receiving, by said transparency software application from said first user, a selection for a plurality of subsequent filter criteria;
second evaluating, by said transparency software application in succession, each of said plurality of subsequent filter criteria;
generating, by said transparency software application, a report indicating results of said first evaluating and said second evaluating; and
storing, by said computing device, said report.
The present invention provides a method comprising:
receiving, by a computing device from an application server, a copy of an application framework;
retrieving, by said computing device from an engine repository, a plurality of reusable software engine implementations;
receiving, by said computing device from an application developer, first application software code associated with said plurality of reusable software engine implementations;
retrieving, by said computing device from a software component repository, a plurality of reusable software component implementations;
receiving, by said computing device from said application developer, second application software code associated with said plurality of reusable software component implementations;
receiving, by said computing device from said application developer, third application software code associating said plurality of reusable software component implementations and said plurality of reusable software engine implementations with a plurality of databases, wherein said plurality of databases comprise requirements for implementing said plurality of reusable software component implementations and said plurality of reusable software engine implementations;
receiving, by said computing device from said application developer, fourth application software code associated with a plurality of locally or remotely accessible application services;
generating, by a computer processor of said computing device, a transparency software application comprising said first application software code, said second application software code, said third application software code, and said fourth application software code; and
storing, by said computing device, said transparency software application.
The present invention advantageously provides a method and associated system capable of generating code.

DETAILED DESCRIPTION OF THE INVENTION

Figure 1:
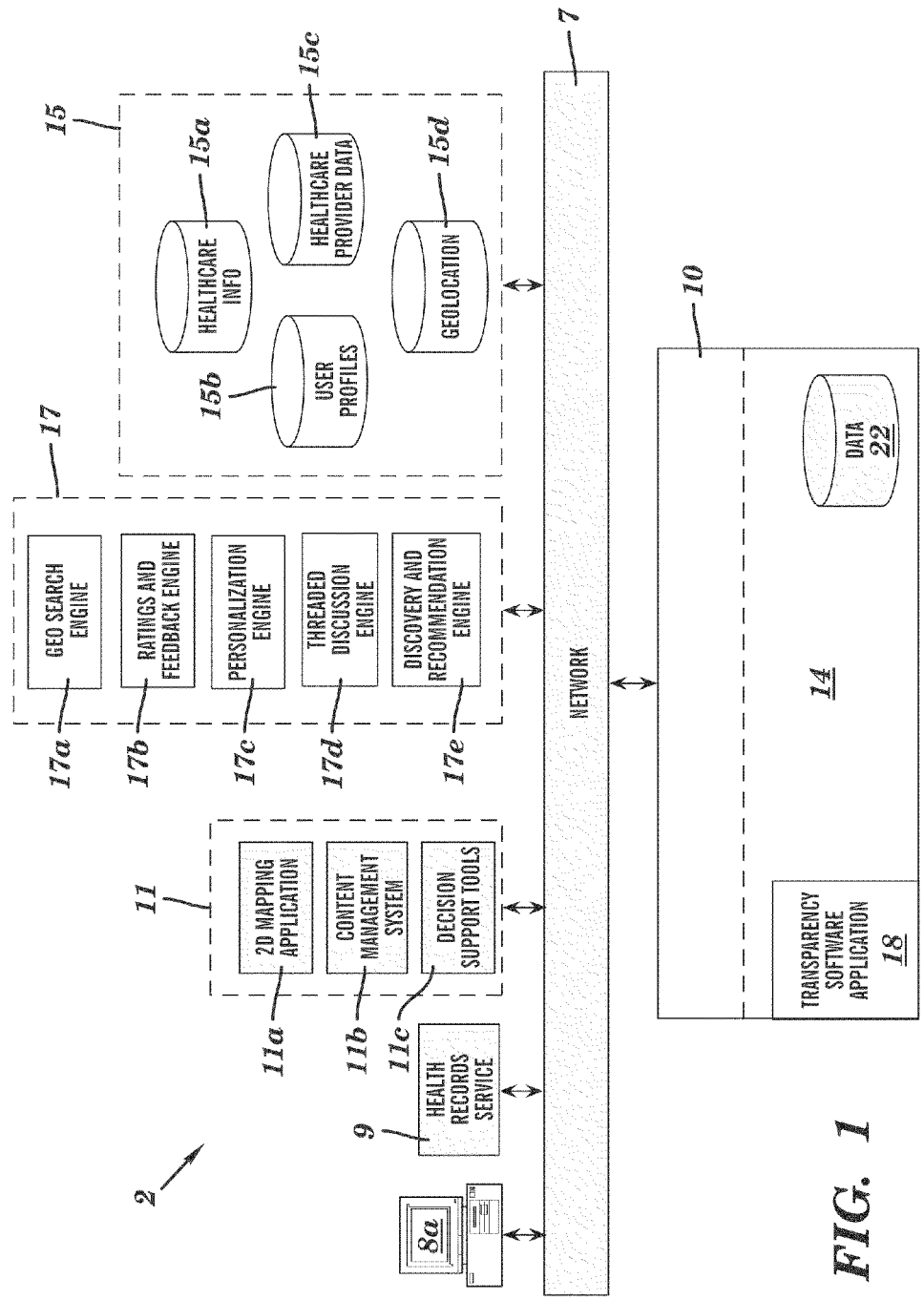
FIG. 1 illustrates a system for implementing a transparency software application, in accordance with embodiments of the present invention.

FIG. 1 illustrates a system 2 for implementing a transparency software application 18, in accordance with embodiments of the present invention. System 2 may comprise an application framework. System 2 performs a process for allowing end users to filter and map data (i.e., from organizations such as, inter alia, health care organizations and government organizations) using multiple nested filter criteria based on various concepts (e.g., health care consumer concepts). The resulting filtered and mapped data may be augmented by integrating a display into an interactive table structure with additional data sets that allow the end users to perform multiple comparison functions. For example, comparison functions may include, inter alia, comparisons of cost, quality, outcomes, geographical distance, ratings, feedback, profiles, etc in a single interactive web user interface. Additionally, transparency software application 18 allows end user to rate individual entities (e.g., health care providers), view average ratings from additional entities (e.g., additional health care consumers), and access a recommendation engine that suggests content (e.g., health information content) based on contextual data found within system 2 (e.g., an application framework).

System 2 comprises a framework for implementing government healthcare transparency with web-accessible networked applications based the following reusable components:

1. A geographical two-dimensional map.
2. A method for contextual and relevant filtering of geographical-based search results.
3. Relevant sets of interactive comparison tables containing quality and cost information aggregated from multiple disparate government sources.
4. Relevant static and dynamic data associated with a user's health condition.
5. Interactive social networking facilities for: managing a user's friends, viewing and providing healthcare consumer feedback and consumer ratings, and participating in threaded discussions.
6. An intelligent discovery and recommendation engine
7. An automatic in-context user profile capture for personalization.
8. A collection of decision support tools.

System 2 of FIG. 1 comprises a network application device(s) 8a (e.g., an I/O device), a health records service 9, an application component system 11, an application engine system 17, and an application database system 15 connected to a computing system 10 through a network 7. Network application device(s) 8a is used by an associated user for accessing computing system 10. Network application device(s) 8a may comprise any type of application device such as, inter alia, a notebook computer, a desktop computer, a personal digital assistant (PDA), etc. Network 7 may comprise any type of network including, inter alia, a local area network, (LAN), a wide area network (WAN), the Internet, etc. Computing system 10 may comprise any type of computing system(s) including, inter alia, a personal computer (PC), a server computer, a database computer, etc. Computing system 10 comprises a memory system 14. Memory system 14 comprises a transparency software application 18 and data 22. Network application device(s) 8a may access the following functions provided by transparency software application 18:

1. The presentation of healthcare information knowledge.
2. The ability to search, filter, and compare geographically scoped healthcare provider services and/or social networking features.

Application component system 11 comprises a two dimensional mapping application 11a, a content management system 11b, and decision support tools 11c. Application engine system 17 comprises a geo-search engine 17a, a ratings and feedback engine 17b, a personalization engine 17c, a threaded discussion engine 17d, and a discovery and recommendation engine 17e. Application database system 15 comprises a healthcare information database 15a, a user profile database 15b, a healthcare provider database 15c, and a geo-location database 15d.

Transparency software application 18 accesses content management system 11b and healthcare information database 15a in order to present relevant healthcare information knowledge. Transparency software application 18 uses:

1. Two dimensional mapping application 11a, geo-location database 15d, healthcare provider database 15c, and user profile database 15b to display a geographical map, allow a user to search, filter, and compare healthcare provider services, and display user-contextual related information.
2. The services from health records service 9.
3. Ratings and feedback engine 17b for displaying and managing user ratings and feedback.
4. Personalization engine 17c for capturing and managing user personalization information.
5. Threaded discussion engine 17d for displaying and managing threaded discussions among users, administrators, and moderators.
6. Discovery and recommendation engine 17e for discovering related user, service, and knowledge information and for providing relevant recommendations in real time.

Transparency software application 18 performs a process for allowing end users to filter and map data in accordance with the following implementation example. In this example, a user is equipped with one or more network application devices (e.g., network application device 8a) and connects to the transparency software application 18 via network 7. The following process associated with transparency software application is performed:

1. The user prompts transparency software application 18 to retrieve the user's personalized data from personalization engine 17c (e.g., including his/her geographic, demographic, and health profiles) and the user's electronic health records from health records service 9.
2. Transparency software application 18 prompts the user for an address of a point of interest and uses that address to invoke two dimensional mapping application 11a to draw a geographical map centered on the address along with markers on the map representing relevant healthcare service providers whose geo-coded addresses and other metadata is stored in one of the databases in application database system 15.
3. Two dimensional mapping application 11 uses functions provided by geo-search engine 17a and application database system 15 to search, retrieve, and display the geographical map. Additionally, transparency software application 18 accesses ratings and feedback engine 17b to retrieve and display any available ratings and feedback associated with each service provider displayed on the map and selected by the user in order to compare services, cost, and quality of each available service.
4. The user applies various filters made available by transparency software application 18 to show or hide a subset of the service providers located near the currently supplied address.
5. Transparency software application 18 accesses discovery and recommendation engine 17e to evaluate the selected filter criteria, the user's personalized data, and related ratings and feedback in order to search for relevant and useful services and service providers to provide recommendations. Additionally, transparency software application 18 generates a table illustrating the cost and quality comparison of the currently selected services and service providers.

System 2 (e.g., an application framework) provides patterns and interfaces for implementing a general healthcare transparency application (e.g., transparency software application 18) with a two dimensional mapping application 11a, content management system 11b, and decision support tools 11c. Each component of application engine system 17 and application database system 15 comprises a pluggable component that may be removed and replaced with compatible replacement components as long as they implement the framework specified application engine interfaces and/or database access services. System 2 uses a service mash-up method to orchestrate, utilize, and combine services of the pluggable engines and databases to compose and implement the healthcare transparency application instance.

Figure 2:
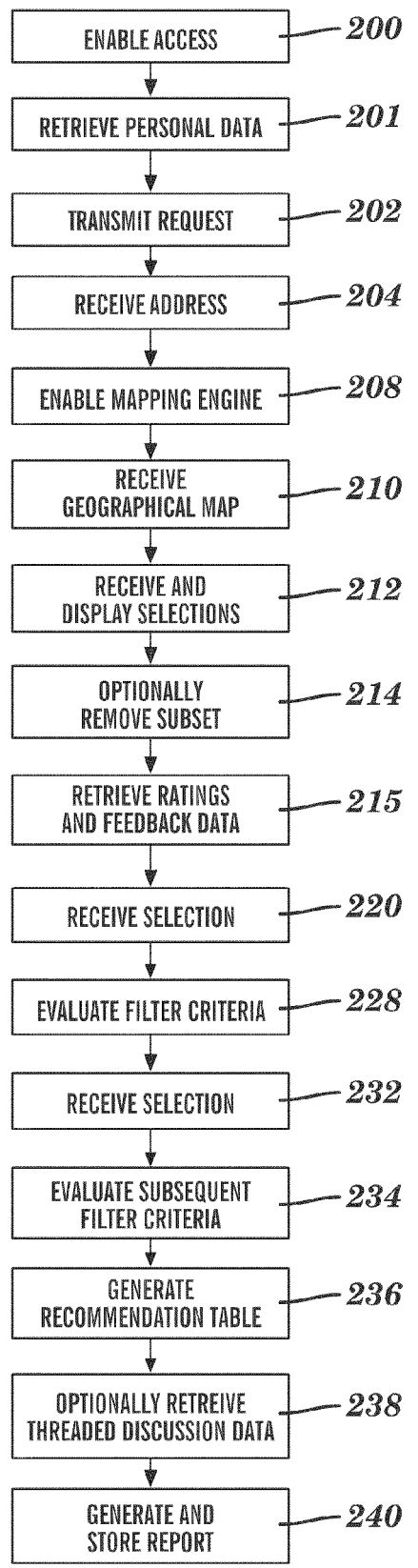
FIG. 2 illustrates a flowchart describing an algorithm used by the system of FIG. 1 for allowing end users to filter and map data using multiple nested filter criteria based on various concepts, in accordance with embodiments of the present invention.

FIG. 2 illustrates a flowchart describing an algorithm used by system 2 of FIG. 1 for allowing end users to filter and map data using multiple nested filter criteria based on various concepts, in accordance with embodiments of the present invention. In step 200, a computing device (e.g., computing system 10 in FIG. 1) enables (i.e., for a user) access to a transparency software application (e.g., transparency software application 18 in FIG. 1. In step 201, the transparency software application retrieves (i.e., from a personalization engine such as personalization engine 17c in FIG. 1) personal data associated with the user (e.g., geographic data, demographic data, and health profile data). In step 202, the transparency software application transmits (to the user) a first request for a point of interest associated with the user. In step 204, the transparency software application receives (i.e., from the user in response to the first request) an address associated with the point of interest. In step 208, the transparency software application enables (i.e., in response to receiving the address) a two dimensional mapping application (e.g., two dimensional mapping application 11a in FIG. 1). In step 210, the transparency software application receives (i.e., from the two dimensional mapping engine) a geographical map associated with the address. The geographical map may comprise markers representing relevant healthcare service providers comprising geo-coded addresses and associated metadata stored in an application database. In step 212, the transparency software application receives (i.e., from the user) selections for relevant healthcare service providers specified on the geographical map. The transparency software application may optionally display the selections for relevant healthcare service providers. In step 214, the transparency software application may optionally remove (i.e., in response to a command from the user) a subset of the relevant healthcare service providers. In step 215, the transparency software application retrieves (i.e., from a ratings and feedback engine) ratings and feedback data associated with the relevant healthcare service providers. The ratings and feedback data may comprise data comparing services, cost, and a quality of each healthcare service provider. In step 220, the transparency software application receives (i.e., from the user) a selection for a first filter criteria. In step 228, the transparency software application evaluates the first filter criteria. In step 232, the transparency software application receives (i.e., from the user) a selection for a plurality of subsequent filter criteria. In step 234, the transparency software application evaluates in succession, the plurality subsequent filter criteria. In step 236, the transparency software application optionally, generates and stores a recommendation table illustrating a cost and quality comparison of the relevant and useful services and the service providers. The transparency software application generates the recommendation table by:
1. Evaluating the personal data and ratings and feedback data.
2. Selecting relevant and useful services and service providers from the relevant healthcare service providers In step 238, the transparency software application optionally retrieves (i.e., from a threaded discussion engine) threaded discussion data generated by users, administrators, and moderators. The threaded discussion data is associated with the relevant healthcare service providers. In step 240, the transparency software application generates and stores a report indicating results of evaluating process of steps 228 and 234.

Figure 3:
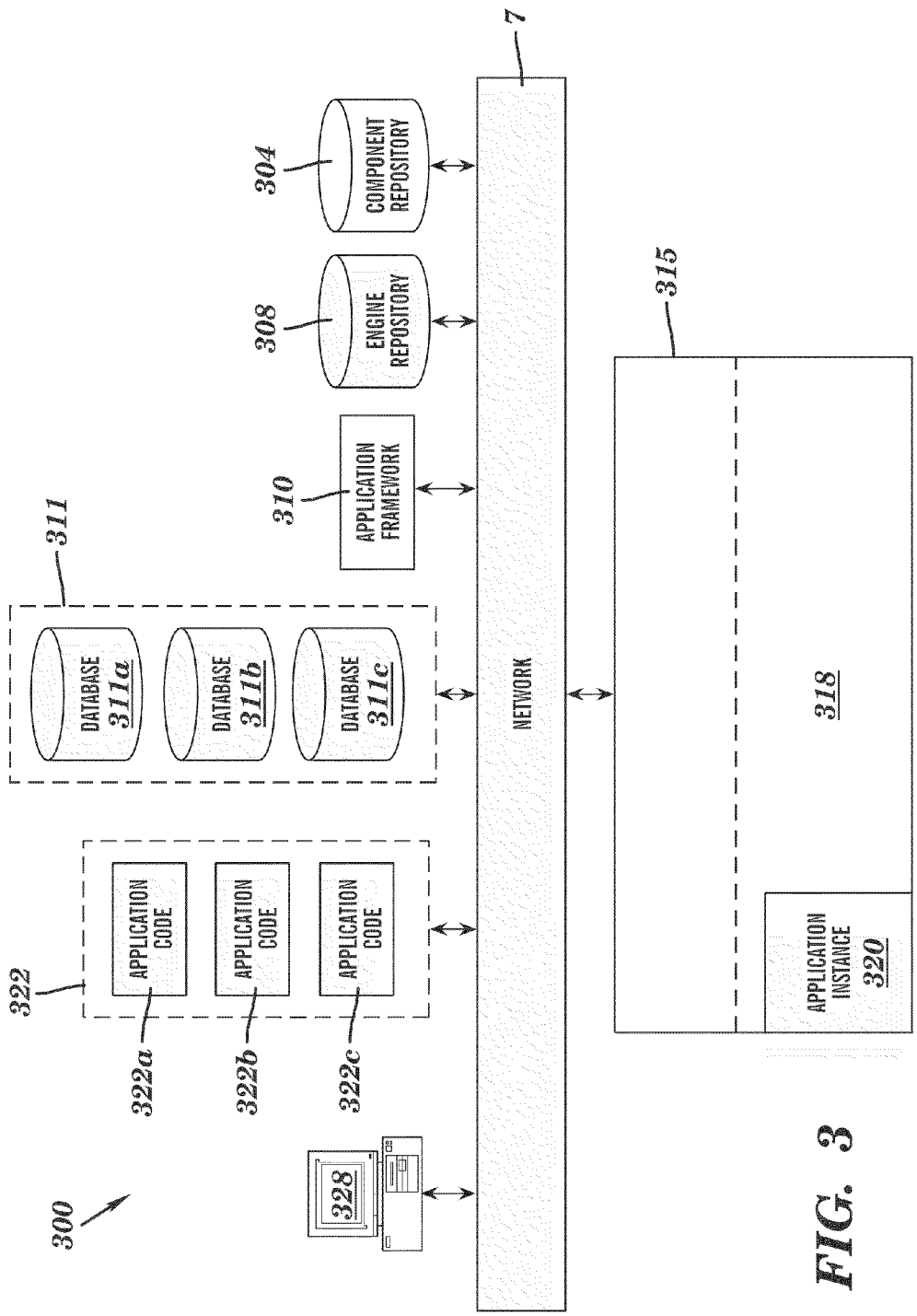
FIG. 3 illustrates a system for generating a transparency software application, in accordance with embodiments of the present invention.

FIG. 3 illustrates a system 300 for generating a specific instance of transparency software application 18 of FIG. 1, in accordance with embodiments of the present invention. System 300 comprises an input/output (I/O) device 328, an application code repository 322 (i.e., comprising application code 322a . . . 322c developed by a user using I/O device 328), a database system 311 (i.e., comprising databases 311a . . . 311c), an application framework 310, an engine repository 308, and a component repository 304 connected to a computing system 315 through a network 7. I/O device 328 is used by an associated user for accessing computing system 315 and generating application code 322a . . . 322c. I/O device 328 may comprise any type of device such as, inter alia, a notebook computer, a desktop computer, a personal digital assistant (PDA), etc. Network 7 may comprise any type of network including, inter alia, a local area network, (LAN), a wide area network (WAN), the Internet, etc. Computing system 315 may comprise any type of computing system(s) including, inter alia, a personal computer (PC), a server computer, a database computer, etc. Computing system 315 comprises a memory system 318. Memory system 318 comprises a generated software application instance 320. The following process is executed by an application developer to create an instance of transparency software application 18 of FIG. 1 for a specific purpose:

1. An application developer instantiates a specific application instance by embedding and extending a copy of application framework 310 in his/her file system workspace (e.g., I/O device 328).
2. The application developer accesses engine repository 308 (i.e., comprising various preexisting reusable engine implementations that provide various functions such as, inter alia, geo-search capabilities or personalization capabilities) in order to retrieve preexisting reusable engine implementations. If a preexisting reusable engine implementation (i.e., that fits a specific set of capability requirements) cannot be found, the application developer creates a new engine implementation (i.e., fitting specified requirements) and places the new engine implementation in engine repository 308 for use by this application and others.
3. The application developer accesses component repository 304 (i.e., comprising various preexisting reusable component implementations that provide various functions such as, inter alia, content management or two dimensional mapping) in order to retrieve preexisting reusable component implementations. If a preexisting reusable component implementation (i.e., that fits a specific set of capability requirements) cannot be found, the application developer creates a new component implementation (i.e., fitting specified requirements) and places the new component implementation in component repository 304 for use by this application and others.
4. The application developer creates application code (e.g., any of application code 322a . . . 322c). The application code associates with and uses selected component capabilities from component repository 304.
5. The application developer creates application code (e.g., any of application code 322a . . . 322c). The application code associates with and uses selected engines capabilities from engine repository 308.
6. The application developer instantiates databases 311a . . . 311c (e.g., a user profile database, a healthcare information database) corresponding to the selected component and engine requirements and creates application code (e.g., any of application code 322a . . . 322c) that associates with and uses databases 311a . . . 311c.
7. The application developer creates application code (e.g., any of application code 322a . . . 322c) that associates with and uses any number of locally accessible or remotely accessible application services (e.g., services that provide access to electronic health records services).

The aforementioned process generates a functioning instance of transparency software application 18 of FIG. 1 thereby meeting specific application requirements and using a reusable application framework, engines, components, application databases, and a collection of local or remote applications.

Figure 4:
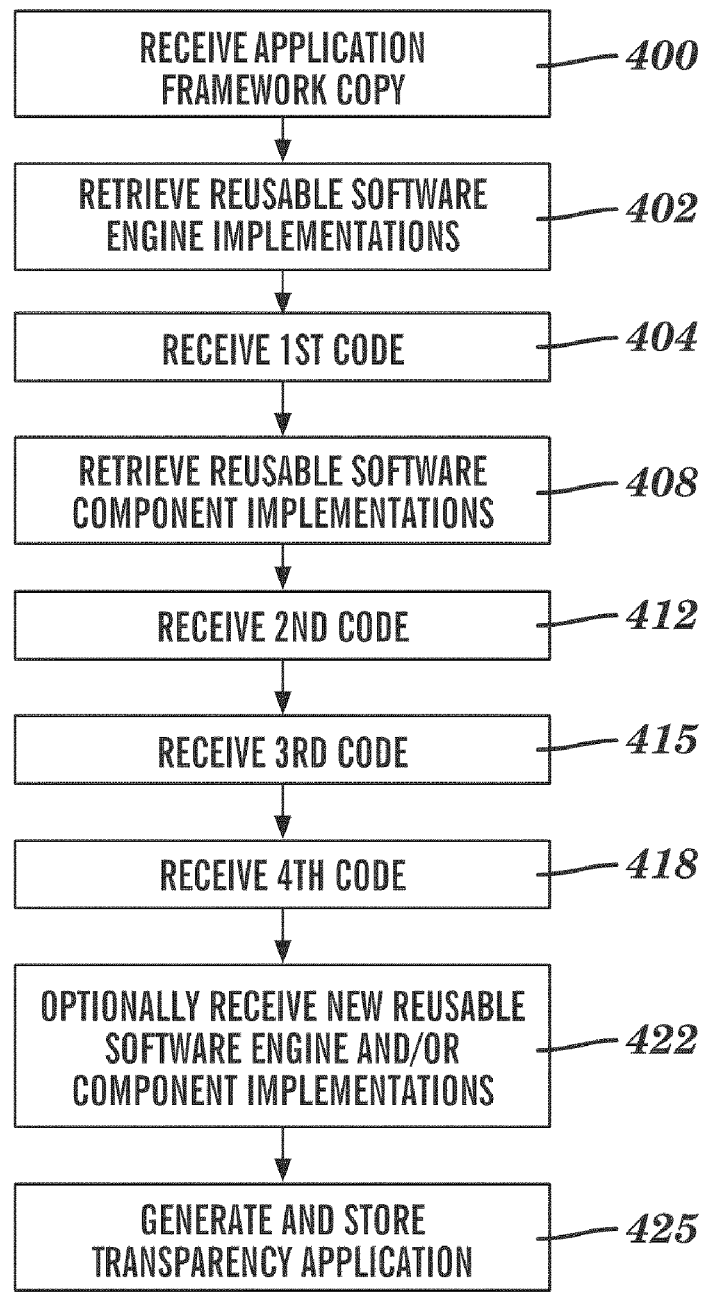
FIG. 4 illustrates a flowchart describing an algorithm used by the system of FIG. 3 for generating a specific instance of the transparency software application of FIG. 1, in accordance with embodiments of the present invention.

FIG. 4 illustrates a flowchart describing an algorithm used by system 300 of FIG. 3 for generating a specific instance of transparency software application 18 of FIG. 1, in accordance with embodiments of the present invention. In step 400, a computing device (e.g., computing system 315 in FIG. 1) receives (i.e., from an application server such as application framework 310 of FIG. 3) a copy of the application framework. In step 402, the computing device retrieves (i.e., from an engine repository) a plurality of reusable software engine implementations. In step 404, the computing device receives (i.e., from an application developer) first application software code associated with the plurality of reusable software engine implementations. In step 408, the computing device retrieves (i.e., from a software component repository) a plurality of reusable software component implementations. In step 412, the computing device receives (i.e., from the application developer) second application software code associated with the plurality of reusable software component implementations. In step 415, the computing device receives (i.e., from the application developer) third application software code associating the plurality of reusable software component implementations and the plurality of reusable software engine implementations with a plurality of databases. The plurality of databases comprise requirements for implementing the plurality of reusable software component implementations and the plurality of reusable software engine implementations. In step 418, the computing device receives (i.e., from the application developer) fourth application software code associated with a plurality of locally or remotely accessible application services. In optional step 422, the computing device receives (i.e., from the application developer):

1. A new reusable software engine implementation associated with a specified set of capability requirements specified by the application developer.
2. A new reusable software component implementation associated with a specified set of capability requirements specified by the application developer.

The new reusable software engine implementation is transmitted to the engine repository for storage. The new reusable software component implementation is transmitted to the component repository for storage. In step 425, the computing device generates and stores the transparency software application comprising the first application software code, the second application software code, the third application software code, and the fourth application software code.

Figure 5:
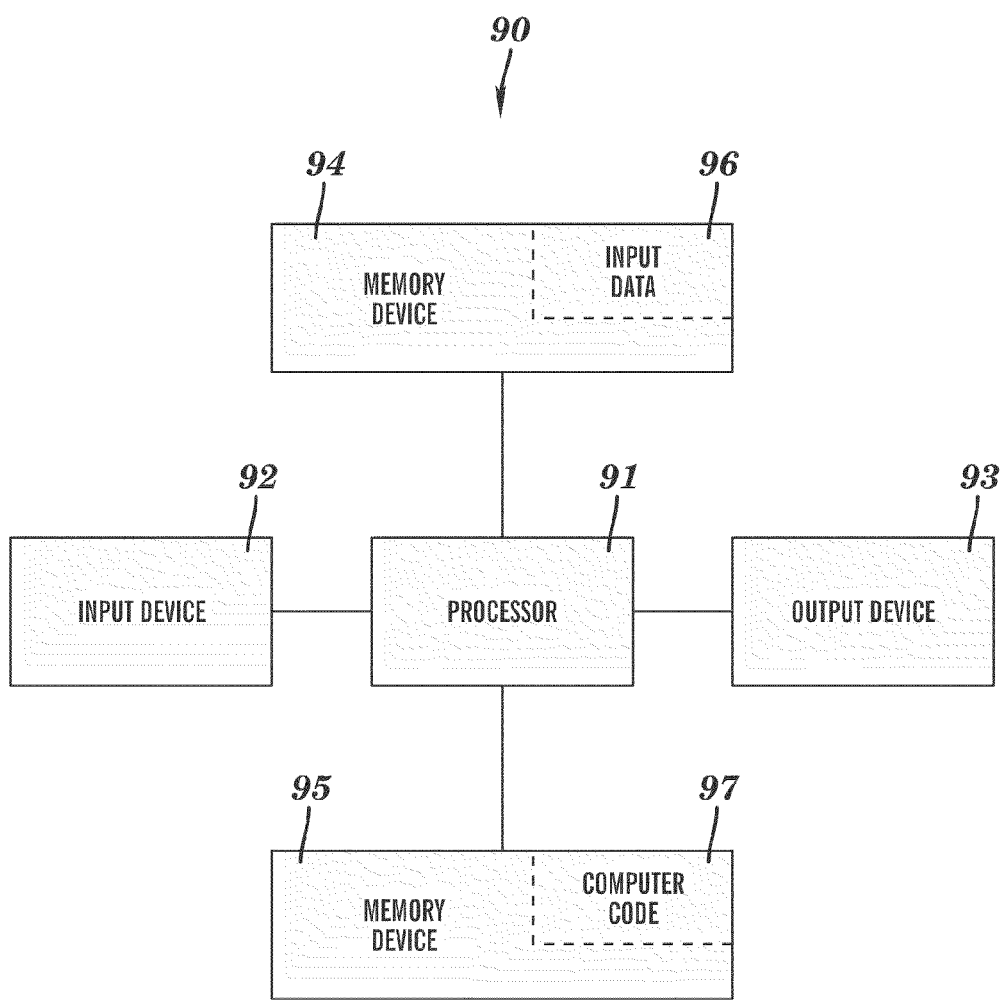
FIG. 5 illustrates a computer apparatus used for generating or implementing a transparency software application, in accordance with embodiments of the present invention.

FIG. 5 illustrates a computer apparatus 90 (e.g., computing system 10 of FIG. 1 or computing system 315 of FIG. 3) used for generating or implementing a transparency software application, in accordance with embodiments of the present invention. The computer system 90 comprises a processor 91, an input device 92 coupled to the processor 91, an output device 93 coupled to the processor 91, and memory devices 94 and 95 each coupled to the processor 91. The input device 92 may be, inter alia, a keyboard, a mouse, etc. The output device 93 may be, inter alia, a printer, a plotter, a computer screen, a magnetic tape, a removable hard disk, a floppy disk, etc. The memory devices 94 and 95 may be, inter alia, a hard disk, a floppy disk, a magnetic tape, an optical storage such as a compact disc (CD) or a digital video disc (DVD), a dynamic random access memory (DRAM), a read-only memory (ROM), etc. The memory device 95 includes a computer code 97. The computer code 97 includes algorithms (e.g., the algorithms of FIGS. 2 and 4) for generating or implementing a transparency software application. The processor 91 executes the computer code 97. The memory device 94 includes input data 96. The input data 96 includes input required by the computer code 97. The output device 93 displays output from the computer code 97. Either or both memory devices 94 and 95 (or one or more additional memory devices not shown in FIG. 5) may comprise the algorithms of FIG. 2 and FIG. 4 and may be used as a computer usable medium (or a computer readable medium or a program storage device) having a computer readable program code embodied therein and/or having other data stored therein, wherein the computer readable program code comprises the computer code 97. Generally, a computer program product (or, alternatively, an article of manufacture) of the computer system 90 may comprise said computer usable medium (or said program storage device).

Still yet, any of the components of the present invention could be created, integrated, hosted, maintained, deployed, managed, serviced, etc. by a service provider who offers to generate or implement a transparency software application. Thus the present invention discloses a process for deploying, creating, integrating, hosting, maintaining, and/or integrating computing infrastructure, comprising integrating computer-readable code into the computer system 90, wherein the code in combination with the computer system 90 is capable of performing a method for generating or implementing a transparency software application. In another embodiment, the invention provides a business method that performs the process steps of the invention on a subscription, advertising, and/or fee basis. That is, a service provider, such as a Solution Integrator, could offer to generate or implement a transparency software application. In this case, the service provider can create, maintain, support, etc. a computer infrastructure that performs the process steps of the invention for one or more customers. In return, the service provider can receive payment from the customer(s) under a subscription and/or fee agreement and/or the service provider can receive payment from the sale of advertising content to one or more third parties.

While FIG. 5 shows the computer system 90 as a particular configuration of hardware and software, any configuration of hardware and software, as would be known to a person of ordinary skill in the art, may be utilized for the purposes stated supra in conjunction with the particular computer system 90 of FIG. 5. For example, the memory devices 94 and 95 may be portions of a single memory device rather than separate memory devices.

While embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A method comprising:
    enabling, by a computing device for a first user, access to a transparency software application, said transparency software application executed by a computer processor of said computing device;
    retrieving, by said transparency software application from a personalization engine, personal data associated with said first user;

transmitting, by said transparency software application to said first user, a first request for a point of interest associated with said first user;

receiving, by said transparency software application from said first user in response to said first request, an address associated with said point of interest;

receiving, by said transparency software application from aggregated multiple disparate government sources, relevant sets of interactive comparison tables comprising medical quality and cost information;

retrieving, by said transparency software application from said personal information, relevant static and dynamic data associated with a health condition of said first user;

receiving, by said transparency software application from interactive social networking facilities, healthcare consumer feedback and consumer ratings from users, administrators, and moderators participating in threaded discussions;

enabling, by said transparency software application in response to said receiving said address, a two dimensional mapping application;

receiving, by said transparency software application from said two dimensional mapping application, a geographical map associated with said address;

receiving, by said transparency software application from said first user, selections for relevant healthcare service providers specified on said geographical map;

retrieving, by said transparency software application from a ratings and feedback engine, ratings and feedback data associated with said relevant healthcare service providers;

receiving, by said transparency software application from said first user, a selection for a first filter criteria;

first evaluating, by said transparency software application, said first filter criteria;

receiving, by said transparency software application from said first user, a selection for a plurality of subsequent filter criteria;

second evaluating, by said transparency software application in succession, each of said plurality of subsequent filter criteria;

third evaluating, said relevant sets of interactive comparison tables, said relevant static and dynamic data, and said healthcare consumer feedback and consumer ratings;

generating, by said transparency software application, a report indicating results of said first evaluating, said second evaluating, and said third evaluating; and storing, by said computing device, said report.

2. The method of claim 1, wherein said personal data associated with said first user comprises geographic data, demographic data, and health profile data.

3. The method of claim 1, wherein said geographical map comprises markers representing said relevant healthcare service providers comprising geo-coded addresses and associated metadata stored in an application database.

4. The method of claim 1, wherein said ratings and feedback data comprises data comparing services, cost, and a quality of each healthcare service provider of said relevant healthcare service providers.

5. The method of claim 4, further comprising:
displaying, by said transparency software application, said selections for said relevant healthcare service providers and said ratings and feedback data.

6. The method of claim 4, further comprising:
removing, by said transparency software application in response to a command from said first user, a subset of said relevant healthcare service providers.

7. The method of claim 1, further comprising:
evaluating, by said transparency software application, said personal data and said ratings and feedback data;
selecting, by said transparency software application, relevant and useful services and service providers from said relevant healthcare service providers;
generating, by said transparency software application, a recommendation table illustrating a cost and quality comparison of said relevant and useful services and said service providers; and
storing, by said computing device, said recommendation table.

8. The method of claim 1, further comprising:
retrieving, by said transparency software application from a threaded discussion engine, threaded discussion data generated by users, administrators, and moderators, wherein said threaded discussion data is associated with said relevant healthcare service providers, and wherein said report comprises said threaded discussion data.

9. A process for supporting computer infrastructure, said process comprising providing at least one support service for at least one of creating, integrating, hosting, maintaining, and deploying computer-readable code in said computing device, wherein the code in combination with said computing device is capable of performing the method of claim 1.

10. A computer program product, comprising a computer storage medium comprising a computer readable program code embodied therein, said computer readable program code configured to perform the method of claim 1 upon being executed by said computer processor of said computing device.

11. A computing system comprising a processor coupled to a computer-readable memory unit, said memory unit comprising a computer readable code configured to be executed by the processor to perform the method of claim 1.

12. A method comprising:
receiving, by a computing device from an application server, a copy of an application framework;
retrieving, by said computing device from an engine repository, a plurality of reusable software engine implementations consisting of a geo-search engine implementation, a ratings and feedback engine implementation, a personalization engine implementation, a threaded discussion engine implementation, and a discovery and recommendation engine implementation;
receiving, by said computing device from an application developer, first application software code associated with said plurality of reusable software engine implementations;
retrieving, by said computing device from a software component repository, a plurality of reusable software component implementations consisting of a two dimensional mapping application implementation, a content management system implementation, and a decision support tool implementation;
receiving, by said computing device from said application developer, second application software code associated with said plurality of reusable software component implementations;
receiving, by said computing device from said application developer, third application software code associating said plurality of reusable software component implementations and said plurality of reusable software engine implementations with a plurality of databases, wherein said plurality of databases comprise requirements for implementing said plurality of reusable software component implementations and said plurality of reusable software engine implementations, and wherein said plurality of databases consist of a healthcare information database, a user profile database, a healthcare provider database, and a geo-location database;

receiving, by said computing device from said application developer, fourth application software code associated with a plurality of locally or remotely accessible application services;

generating, by a computer processor of said computing device, a transparency software application comprising said first application software code, said second application software code, said third application software code, and said fourth application software code; and storing, by said computing device, said transparency software application.

13. The method of claim 12, wherein said plurality of reusable software engine implementations provide geo-search capabilities and personalization capabilities.

14. The method of claim 12, further comprising:

receiving, by said computing device from said application developer, a new reusable software engine implementation associated with a specified set of capability requirements specified by said application developer; and transmitting, by said computing device to said engine repository, said new reusable software engine implementation.

15. The method of claim 12, wherein said plurality of reusable software component implementations comprise content management capabilities and 2 dimensional mapping capabilities.

16. The method of claim 12, further comprising:

receiving, by said computing device from said application developer, a new reusable software component implementation associated with a specific set of capability requirements specified by said application developer; and transmitting, by said computing device to said component repository, said new reusable software component implementation.

17. The method of claim 12, wherein said plurality of databases comprise databases associated with user profiles and healthcare information.

18. The method of claim 12, wherein said plurality of locally or remotely accessible application services provide access to electronic health records services.

19. A process for supporting computer infrastructure, said process comprising providing at least one support service for at least one of creating, integrating, hosting, maintaining, and deploying computer-readable code in said computing device, wherein the code in combination with said computing device is capable of performing the method of claim 12.

20. A computer program product, comprising a computer storage medium comprising a computer readable program code embodied therein, said computer readable program code configured to perform the method of claim 12 upon being executed by said computer processor of said computing device.

* * * * *